US009782521B2

(12) United States Patent
Omata et al.

(10) Patent No.: US 9,782,521 B2
(45) Date of Patent: Oct. 10, 2017

(54) MEDICAL DEVICE AND METHOD FOR PRODUCING MEDICAL DEVICE (71) Applicant: TERUMO KABUSHIKI KAISHA, Shibuya-ku, Tokyo (JP)

(72) Inventors: Kazuya Omata, Fujinomiya (JP); Tomoe Hakamatani, Kanagawa (JP); Takao Anzai, Hiratsuka (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 44 days.

(21) Appl. No.: 14/869,245

(22) Filed: Sep. 29, 2015

(65) Prior Publication Data

US 2016/0015869 A1 Jan. 21, 2016

Related U.S. Application Data (63) Continuation of application No. PCT/JP2014/057406, filed on Mar. 18, 2014.

(30) Foreign Application Priority Data

Apr. 1, 2013 (JP) ................. 2013-075770

(51) Int. Cl.
A61L 31/10 (2006.01)
A61L 29/08 (2006.01)
(Continued)

(52) U.S. Cl.
CPC ............. A61L 31/10 (2013.01); A61L 29/085 (2013.01); A61L 29/14 (2013.01); A61L 31/14 (2013.01);
(Continued)

(58) Field of Classification Search
CPC .......... A61L 31/10; A61L 29/14; A61L 31/14; A61L 29/085; A61L 2420/02; A61L 2400/10; A61L 2420/06; C08L 53/00
See application file for complete search history.

(56) References Cited

U.S. PATENT DOCUMENTS 5,079,093 A 1/1992 Akashi et al.
5,670,558 A 9/1997 Onishi et al.
(Continued)

FOREIGN PATENT DOCUMENTS

EP 0611576 A1 8/1994
EP 0693293 A1 1/1996
(Continued)

OTHER PUBLICATIONS

International Search Report (PCT/ISA/210) mailed on Jun. 17, 2014, by the Japanese Patent Office as the International Searching Authority for International Application No. PCT/JP2014/057406.
(Continued)

Primary Examiner — Taiwo Oladapo
(74) Attorney, Agent, or Firm — Buchanan, Ingersoll & Rooney PC (57) ABSTRACT A medical device including a lubricating coating film (surface lubricating layer) that exerts excellent lubricity and durability is provided. The medical device includes, on a base layer, a surface lubricating layer formed from a block copolymer having a hydrophilic portion and a hydrophobic portion that has a reactive functional group. The ratio of the hydrophobic portion of the block copolymer in an outermost surface of the surface lubricating layer is 20 to 45 mol %, and the viscosity of a 1 wt % chloroform solution of the block copolymer at a temperature of 30° C. is 8 to 30 mPa·s.

21 Claims, 2 Drawing Sheets (51) Int. Cl.
    *A61L 29/14*        (2006.01)
    *A61L 31/14*        (2006.01)
(52) U.S. Cl.
    CPC ....... *A61L 2400/10* (2013.01); *A61L 2420/02* (2013.01); *A61L 2420/06* (2013.01)

(56) References Cited

U.S. PATENT DOCUMENTS

2010/0019189 A1*   1/2010   Kurita ................. A61M 1/1008
                                                       252/62.54
2011/0274918 A1*  11/2011   Omata ................. A61L 29/085
                                                       428/336

FOREIGN PATENT DOCUMENTS

| EP | 2065406 A1 | 6/2009 |
| EP | 2392362 A1 | 12/2011 |
| JP | 08-33704 A | 2/1996 |
| JP | 2007-289299 A | 11/2007 |

OTHER PUBLICATIONS

Extended Search Report issued by the European Patent Office in corresponding European Patent Application No. 14779833.4 on Nov. 7, 2016 (8 pages).

* cited by examiner

MEDICAL DEVICE AND METHOD FOR PRODUCING MEDICAL DEVICE

CROSS-REFERENCES TO RELATED APPLICATIONS

This application is a continuation of International Application No. PCT/JP2013/075770 filed on Apr. 1, 2013, designating the U.S. and claims priority to Japanese Application No. 2013-075770 filed on Apr. 1, 2013, the entire content of which is incorporated herein by reference.

TECHNICAL FIELD

Disclosed is a medical device and a method for producing a medical device.

BACKGROUND DISCUSSION

Medical devices to be inserted in vivo, such as catheters, guidewires, indwelling needles and the like, are required to have excellent lubricity in order to reduce tissue damage in blood vessels or the like and also improve the operability for the operator. For this reason, methods for forming a coating of a hydrophilic polymer having lubricity on the surface of a base layer have been developed and put into practical use. In such a medical device, the elution/peeling of the hydrophilic polymer from the base layer surface is problematic in terms of maintaining the safety and operability. For this reason, a coating of a hydrophilic polymer is required to have not only excellent lubricity but also durability against loads such as abrasion, scratching and the like.

From such a point of view, PTL 1 discloses a medical device, which is obtained by dissolving a water-soluble or water-swellable polymer in a solvent that swells a base layer of a medical device to produce a polymer solution, immersing a base layer of a medical device in the polymer solution to cause swelling, and further crosslinking or polymerizing the polymer on the base layer surface, thereby forming a surface lubricating layer on the base layer surface.

According to the technique disclosed in PTL 1, a surface lubricating layer having relatively excellent lubricity can be fixed to a base layer.

PTL 1: JP-A-8-33704 (corresponding to U.S. Pat. No. 5,670,558)

SUMMARY

PTL 1 discloses that, as the water-soluble or water-swellable polymer, it is preferable to use a block copolymer having a hydrophilic portion that exhibits lubricity and a portion that has an epoxy group. Further, when such a block copolymer is used, epoxy groups can be crosslinked by a heating operation, whereby a surface lubricating layer that is relatively hard to peel off can be formed. However, there is a trade-off relationship between excellent lubricity and excellent durability, and thus a technique to achieve excellent lubricity and excellent durability at the same time has been demanded.

In particular, in recent years, medical devices have been made significantly smaller and thinner, and a medical procedure in which a medical device approaches a more crooked and narrower lesion area in vivo has been spreading. Accordingly, in order to maintain good device operability even with a complicated lesion area, there has been a demand for a technique to provide the surface of a device with higher lubricity and durability than before.

Therefore, there has been a demand for a technique to improve both lubricity and durability at the same time so as to support medical procedures that are more complicated and advanced.

Against the above background, one object is to provide a medical device including a lubricating coating film (surface lubricating layer) that exerts excellent lubricity and durability. Another object is to provide a method for producing the medical device.

Extensive research has been conducted to solve the problems mentioned above. As a result, it has been found that in a surface lubricating layer formed from a block copolymer having a hydrophilic portion and a hydrophobic portion that has a reactive functional group, when the ratio of the hydrophobic portion of the block copolymer in an outermost surface of the surface lubricating layer is made within a predetermined range, and also the solution viscosity of the block copolymer is made within a predetermined range, the above objects can be achieved.

That is, the first object mentioned above can be achieved by a medical device including, on a base layer, a surface lubricating layer formed from a block copolymer having a hydrophilic portion and a hydrophobic portion that has a reactive functional group. The ratio of the hydrophobic portion of the block copolymer in an outermost surface of the surface lubricating layer is 20 to 45 mol %, and the viscosity of a 1 wt % chloroform solution of the block copolymer at a temperature of 30° C. is 8 to 30 mPa·s. The second object mentioned above can be achieved by a method for producing a medical device, which includes polymerizing a compound including a hydrophilic portion and a compound including a hydrophobic portion that has a reactive functional group in a molar ratio of 20:1 to 50:1 to provide a block copolymer whose 1 wt % chloroform solution has a viscosity of 8 to 30 mP·s at a temperature of 30° C.; preparing a coating liquid containing the block copolymer; and applying the coating liquid onto a base layer, followed by a heating treatment at a temperature within a range of 60 to 200° C., thereby forming a surface lubricating layer having an outermost surface in which the ratio of the hydrophobic portion of the block copolymer is 20 to 45 mol %.

DETAILED DESCRIPTION

According to a first embodiment, provided is a medical device including a surface lubricating layer formed from a block copolymer having a hydrophilic portion and a hydrophobic portion that has a reactive functional group. The ratio of the hydrophobic portion of the block copolymer in an outermost surface of the surface lubricating layer is 20 to 45 mol %, and the viscosity of a 1 wt % chloroform solution of the block copolymer at a temperature of 30° C. is 8 to 30 mPa·s. The first embodiment provides a medical device including a lubricating coating film (surface lubricating layer) that exerts excellent lubricity and durability.

Incidentally, as used herein, "X to Y" representing a range means "X or more and Y or less."

In addition, the phrases "outermost surface of a surface lubricating layer" and "outermost surface" specifically refer to a region 2 nm deep from a surface opposite to the base layer side in the thickness direction of the surface lubricating layer. In addition, the ratio of the hydrophobic portion in an outermost surface is a value calculated by measuring the elemental composition of the outermost surface by XPS (X-ray photoelectron spectroscopy), and represents a ratio measured by the method described below in the Examples. Furthermore, in the outermost surface of the surface lubricating layer, the total amount of the hydrophilic portion and the hydrophobic portion is 100 mol %. As used herein, "weight", "weight (wt) %", and "part by weight" are treated as synonyms of "mass" "mass (mass) %", and "part by mass", respectively.

The disclosed medical device is characterized in that in the outermost surface of a surface lubricating layer formed from a block copolymer having a hydrophilic portion and a hydrophobic portion, the ratio of the hydrophobic portion is within the above range, and also the solution viscosity of the block copolymer under specific conditions is within the above range.

When the ratio of the hydrophilic portion in the block copolymer is increased (i.e., when the ratio of the hydrophobic portion is reduced), although the lubricity (lubricity when wet; hereinafter, "lubricity" means "lubricity when wet" unless otherwise noted) can be improved, the durability decreases. However, it has been found that, as mentioned above, when a block copolymer having high solution viscosity is used, it is possible to form a surface lubricating layer capable of maintaining excellent lubricity without losing durability.

That is, when the ratio of the hydrophilic portion of the block copolymer in the outermost surface of a surface lubricating layer is 55 to 80 mol %, the lubricity is improved over a conventional surface lubricating layer, and also when the solution viscosity of the block copolymer is within the above range, a surface lubricating layer having excellent durability can be formed.

A method for producing a medical device including such a surface lubricating layer will be described below in detail. However, for example, it can be produced by a method in which a compound including a hydrophilic portion and a compound including a hydrophobic portion that has a reactive functional group are mixed and polymerized in an appropriate ratio to give a block copolymer having the above solution viscosity, and then a base layer is coated with the block copolymer, following by a heating treatment in a predetermined temperature range.

The mechanism that the disclosed medical device can achieve excellent durability and lubricity appears to be as follows, but it is to be understood that the medical device is not limited by this apparent mechanism.

In a surface lubricating layer formed from a block copolymer having a hydrophilic portion and a hydrophobic portion, the hydrophilic portion and the hydrophobic portion of the block copolymer are not uniformly distributed, but a larger amount of hydrophobic portion is distributed near the outermost surface. That is, the hydrophobic portion is condensed near the outermost surface of the surface lubricating layer. This is because the energy is more stabilized with a larger amount of hydrophobic portion present in the outermost surface of a surface lubricating layer, which is the interface with air.

The condensation of the hydrophobic portion near the outermost surface becomes more remarkable as the heating treatment temperature is increased. This appears to be because the heating treatment increases the mobility of the block copolymer, which facilitates the movement of the molecular chains, making it easier for the hydrophobic portion to move closer to the outermost surface.

However, when the ratio of the hydrophobic portion in the outermost surface of a surface lubricating layer increases, the lubricity decreases. Specifically, when the ratio of the hydrophobic portion of the block copolymer in the outermost surface of a surface lubricating layer is more than 45 mol %, the ratio of the hydrophilic portion in the surface lubricating layer is insufficient, making it difficult to obtain excellent lubricity. However, excellent lubricity can be obtained when the ratio is equal to or less than 45 mol %. Meanwhile, when the ratio of the hydrophobic portion of the block copolymer in the outermost surface of a surface lubricating layer is less than 20 mol %, the ratio of the hydrophilic portion is so high that it is difficult to obtain durability, such as adhesion to the base layer or the like. It has therefore been found that when the ratio of the hydrophobic portion of a block copolymer in an outermost surface of a surface lubricating layer is 20 to 45 mol %, excellent lubricity and durability can be obtained.

With respect to durability, in order to firmly fix the block copolymer onto the base layer, it is preferable that after the base layer is coated with the block copolymer (lubricating coating agent coating step), the coating is subjected to a heating treatment (heating step). As a result of such a heating treatment, the reactive functional group contained in the hydrophobic portion undergoes a crosslinking reaction, and a firm lubricating coating film (surface lubricating layer) can be formed.

However, as mentioned above, when a heating treatment is performed, the molecular chains are made mobile by heating, and the hydrophobic portion is condensed in the outermost surface, whereby the lubricity tends to decrease. Therefore, the ratio of the hydrophilic portion of the block copolymer to form a surface lubricating layer (i.e., of a block copolymer with which a base layer is coated and which has not been subjected to a heating treatment) is moderately increased. As a result, the condensation of the hydrophobic portion in the surface of a surface lubricating layer due to a heating treatment can be suppressed.

In general, when the ratio of the hydrophilic portion of a block copolymer increases (i.e., when the ratio of the hydrophobic portion decreases), it tends to be difficult to obtain a lubricating coating film (hereinafter sometimes simply referred to as "coating film") with the desired strength, resulting in a decrease in durability. However, it has been found that when a block copolymer having a solution viscosity within an appropriate range (specifically, the viscosity of its 1 wt % chloroform solution is 8 to 30 mPa·s in at a temperature of 30° C.) is used, because of the entanglement of molecular chains, a firm coating film can be formed, and a decrease in durability can be suppressed.

Therefore, the solution viscosity of the block copolymer is made within an appropriate range so as to ensure durability. That is, it possible to provide a medical device including a surface lubricating layer that has excellent lubricity as a result of the moderate reduction of the ratio of the hydrophobic portion (moderate increase of the ratio of the hydrophilic portion) and also has excellent durability at the same time. However, as noted above, the above mechanism is presumption and does not limit the scope of the disclosed medical device or method in any way.

Specifically, it is preferable that the medical device is produced by the following method. That is, according to a second object, provided is a method for producing a medical device, which includes polymerizing a compound including a hydrophilic portion and a compound including a hydrophobic portion that has a reactive functional group in a molar ratio of 20:1 to 50:1 to give a block copolymer whose 1 wt % chloroform solution has a viscosity of 8 to 30 mPa·s at a temperature of 30° C.; preparing a coating liquid containing the block copolymer; and applying the coating liquid onto a base layer, followed by a heating treatment at a temperature within a range of 60 to 200° C., thereby forming a surface lubricating layer having an outermost surface in which the ratio of the hydrophobic portion of the block copolymer is 20 to 45 mol %. According to the disclosed method, a medical device including a lubricating coating film (surface lubricating layer) that exerts excellent lubricity and durability can be provided.

As mentioned above, when the ratio of the hydrophobic portion in the block copolymer used to form a surface lubricating layer is moderately reduced (the ratio of the hydrophilic portion is moderately increased) and the solution viscosity thereof is made within an appropriate range, and further a heating treatment is performed in an appropriate temperature range, excellent lubricity and durability can be exhibited without needlessly increasing the ratio of the hydrophobic portion present in the outermost surface of a lubricating layer after the heating operation.

Hereinafter, illustrative embodiments will be described.

Hereinafter, preferred embodiments of the disclosed medical device will be described with reference to the attached drawings.

Figure 1:
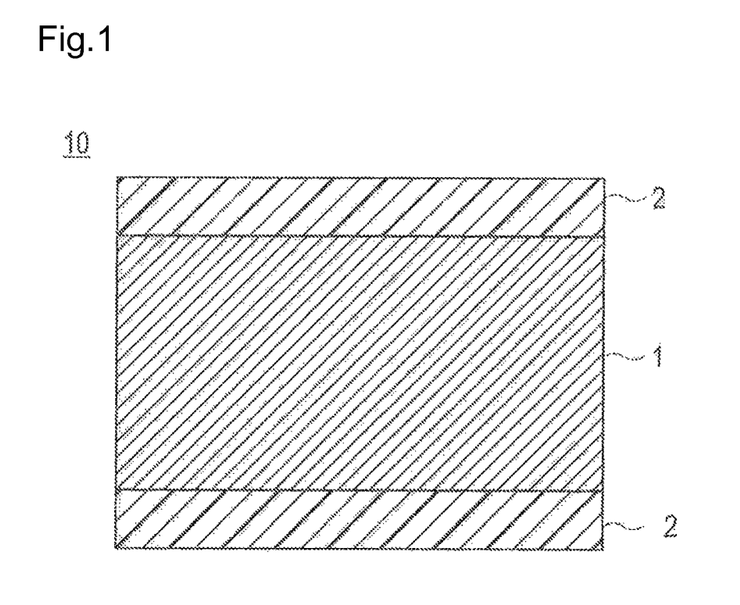
FIG. 1 is a partial sectional view schematically showing a surface laminated structure of one embodiment of the disclosed medical device.
Figure 2:
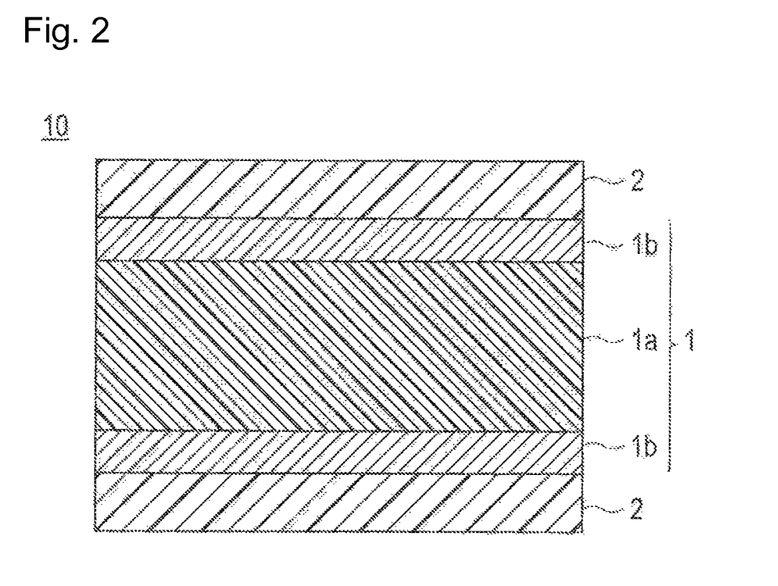
FIG. 2 is a partial sectional view schematically showing another configuration example of a surface laminated structure as an application example of the embodiment of FIG. 1.

FIG. 1 is a partial sectional view schematically showing a surface laminate structure of an illustrative embodiment of the medical device (hereinafter sometimes simply referred to as "medical device"). FIG. 2 is a partial sectional view schematically showing another configuration example of a surface laminate structure as an application example of this embodiment. Incidentally, the reference numerals in FIG. 1 and FIG. 2 represent the following elements. Reference numeral 1 is a base layer; reference numeral 1a is a base layer core part; reference numeral 1b is a base surface layer; reference numeral 2 is a surface lubricating layer; and reference numeral 10 is an exemplary medical device.

As shown in FIG. 1 and FIG. 2, the medical device 10 of this embodiment includes the base layer 1 and the surface lubricating layer 2 that is provided on at least part of the base layer 1 (in the illustrated example, it is provided entirely on the surface of the base layer 1 (entire surface) in the figure) and contains a block copolymer.

Hereinafter, the components of the medical device of this embodiment will each be described in detail.

The base layer used in this embodiment may be made of any material, and materials therefor are not particularly limited. Specific examples of materials to form the base layer 1 include metal materials, polymer materials, ceramics and the like. Here, the base layer 1 may be configured such that the entire base layer 1 is made of one of the above materials. Alternatively, as shown in FIG. 2, it may also be configured such that the surface of the base layer core part 1a made of one of the above materials is covered with another one of the above materials by an appropriate method to form the base surface layer 1b. Examples in the latter case include those configured such that the surface of the base layer core part 1a made of a polymer material or the like is covered with a metal material by an appropriate method (a conventionally known method such as plating, metal deposition, sputtering or the like) to form the base surface layer 1b; or the surface of the base layer core part 1a made of a hard reinforcing material, such as a metal material, a ceramic material or the like, is covered with a polymer material that is flexible as compared with the metal material or like reinforcing material by an appropriate method (a conventionally known method such as immersion (dipping), atomization (spraying), application/printing) or the like, or a reinforcing material forming the base layer core part 1a is composited with a polymer material, thereby forming the base surface layer 1b. In addition, the base layer core part 1a may be a multilayered structure having a laminate of multiple layers of different materials, or may be a structure having members made of different materials for different parts of the medical device and joined together, for example. In addition, it is possible that a middle layer (not illustrated) made of still another one of the above materials is formed between the base layer core part 1a and the base surface layer 1b. Further, also with respect to the base surface layer 1b, it may be a multilayered structure having a laminate of multiple layers of different materials, or may be a structure having members made of different materials for different parts of the medical device and joined together, for example.

Among materials for forming the base layer 1, metal materials are not particularly limited, and metal materials generally used for medical devices such as catheters, guidewires, indwelling needles and the like are used. Specific examples thereof include various stainless steels such as SUS304, SUS316, SUS316L, SUS420J2, SUS630 and the like, gold, platinum, silver, copper, nickel, cobalt, titanium, iron, aluminum, tin, various alloys such as a nickel-titanium alloy, a nickel-cobalt alloy, a cobalt-chrome alloy, a zinc-tungsten alloy and the like. They may be used alone, and it is also possible to use two or more kinds together. As the metal material, a metal material that is optimal for a base layer for the intended use, that is, a catheter, a guidewire, an indwelling needle, or the like, should be suitably selected.

The materials for forming the base layer 1, polymer materials are not particularly limited, and polymer materials generally used for medical devices such as catheters, guidewires, indwelling needles and the like may be used. Specific examples thereof include a polyamide resin, polyolefin resins such as a polyethylene resin, a polypropylene resin and the like, a modified polyolefin resin, a cyclic polyolefin resin, an epoxy resin, an urethane resin, a diallyl phthalate resin (an allyl resin), a polycarbonate resin, a fluororesin, amino resins (a urea resin, a melamine resin, a benzoguanamine resin), a polyester resin, a styrol resin, an acrylic resin, a polyacetal resin, a polyvinyl acetate resin, a phenol resin, a vinyl chloride resin, a silicone resin (a silicon resin), a polyether resin, a polyimide resin, and the like. They may be used alone, and it is also possible to use two or more kinds together. As the polymer material, a polymer material that is optimal for a base layer for the intended use, that is, a catheter, a guidewire, an indwelling needle, or the like, should be suitably selected.

The base layer is not particularly limited in shape and may be in the shape of a sheet, a linear(wire), a tube, or the like suitably selected according to the mode of use.

The disclosed medical device includes a surface lubricating layer formed from a block copolymer on the base layer (base layer). Hereinafter, the block copolymer used to form a surface lubricating layer will be described.

The disclosed block copolymer is a block copolymer having a hydrophilic portion and a hydrophobic portion that has a reactive functional group. Specifically, the block copolymer can be obtained by copolymerizing a monomer including a hydrophilic portion and a monomer including a hydrophobic portion that has a reactive functional group.

The hydrophilic portion of the block copolymer results from the polymerization of a monomer including a hydrophilic portion (sometimes referred to as "hydrophilic monomer" herein). The hydrophilic monomer may be any monomer as long as it exhibits lubricity in a body fluid or an aqueous solvent.

Examples of hydrophilic monomers include acrylic acid, methacrylic acid, N-methylacrylamide, N,N-dimethylacrylamide (DMAA), acrylamide, acryloylmorpholine, N,N-dimethylamino ethyl acrylate, vinylpyrrolidone, 2-methacryloyloxyethyl phosphorylcholine, 2-methacryloyloxyethyl-D-glycoside, 2-methacryloyloxyethyl-D-mannoside, vinyl methyl ether, 2-hydroxyethyl(meth)acrylate, 4-hydroxybutyl(meth)acrylate, 2-hydroxypropyl(meth)acrylate, 2-hydroxybutyl(meth)acrylate, 6-hydroxyhexyl(meth)acrylate, 1,4-cyclohexanedimethanol mono(meth)acrylate, 1-chloro-2-hydroxypropyl(meth)acrylate, diethylene glycol mono (meth)acrylate, 1,6-hexanediol mono(meth)acrylate, pentaerythritol tri(meth)acrylate, dipentaerythritol penta(meth)acrylate, neopentyl glycol mono(meth)acrylate, trimethylolpropane di(meth)acrylate, trimethylolethane di(meth)acrylate, 2-hydroxy-3-phenoxypropyl(meth)acrylate, 2-hydroxycyclohexyl(meth)acrylate, 4-hydroxycyclohexyl(meth)acrylate, cyclohexanedimethanol mono(meth)acrylate, poly(ethylene glycol)methyl ether acrylate, and poly(ethylene glycol)methyl ether methacrylate. Preferred are N,N-dimethylacrylamide, acrylamide, acrylic acid, methacrylic acid, N,N-dimethylamino ethyl acrylate, 2-hydroxyethyl methacrylate, and vinyl pyrrolidone. These hydrophilic monomers may be used alone, and it is also possible to use a combination of two or more kinds. That is, the hydrophilic portion of the block copolymer may be a homopolymer type formed from a single kind of hydrophilic monomer or a copolymer type formed from two or more kinds of the above hydrophilic monomers. Therefore, it is preferable that the hydrophilic portion is derived from at least one member selected from the group consisting of the above hydrophilic monomers.

(Monomer Including Hydrophobic Portion that has a Reactive Functional Group)

The hydrophobic portion of the block copolymer results from the polymerization of a monomer including a hydrophobic portion that has a reactive functional group (sometimes referred to as "hydrophobic monomer" herein).

The term "reactive functional group" as used herein refers to a functional group that can undergo a crosslinking reaction with another monomer upon a heating treatment, light irradiation, electron irradiation, radiation exposure, plasma irradiation, or the like.

Examples of reactive functional groups include functional groups such as an epoxy group, an isocyanate group, an aldehyde group, an acid halide group, an acid anhydride group and the like. Among them, in terms of the ease of handling, the efficiency of the crosslinking reaction, and the like, it is preferable that the monomer that has a reactive functional group (hydrophobic monomer) is a monomer that has an epoxy group, an isocyanate group, or an aldehyde group, and a monomer that has an epoxy group is particularly preferable. It is possible that only one such reactive functional group is present in the hydrophobic monomer, or it is also possible that a plurality of them are present.

The hydrophobic monomer may be any monomer as long as it has a reactive functional group and is more hydrophobic in a body fluid or an aqueous solvent than at least the hydrophilic monomer used at the time of the production of the block copolymer.

The hydrophobic monomer is not particularly limited as long as it has a reactive functional group. Examples thereof include monomers having an epoxy group in the molecule, such as glycidyl acrylate, glycidyl methacrylate (GMA), allyl glycidyl ether and the like; monomers having an isocyanate group in the molecule, such as (meth)acryloyloxymethyl isocyanate, (meth)acryloyloxyethyl isocyanate and the like; monomers having an aldehyde group in the molecule, such as crotonaldehyde, acrolein, methacrolein and the like; monomers having an acid halide group in the molecule, such as (meth)acryloyl chloride, (meth)acryloyl bromide(meth)acryloyl iodide, and the like; monomers having an acid anhydride group in the molecule, such as maleic anhydride, itaconic anhydride, citraconic anhydride and the like. These hydrophobic monomers may be used alone, and it is also possible to use a combination of two or more kinds. That is, the hydrophobic portion of the block copolymer may be a homopolymer type formed from a single kind of hydrophobic monomer or a copolymer type formed from two or more kinds of the above hydrophobic monomers.

More specific examples of hydrophobic monomers include glycidyl acrylate, glycidyl methacrylate, allyl glycidyl ether, acryloyloxymethyl isocyanate, acryloyloxyethyl isocyanate, methacryloyloxy methyl isocyanate, methacryloyloxy ethyl isocyanate, crotonaldehyde, acrolein, and methacrolein. Therefore, it is preferable that the hydrophobic portion is derived from at least one member selected from the group consisting of the above hydrophobic monomers.

It is preferable that the hydrophobic monomer is at least one member selected from the group consisting of monomers bearing an epoxy group, such as glycidyl acrylate, glycidyl methacrylate and the like, whose reactions are promoted by heat or the like and which are relatively easy to handle.

The disclosed block copolymer has a hydrophilic portion and a hydrophobic portion derived from the above hydrophilic monomer and the above hydrophobic monomer, respectively. Here, the ratio between the hydrophilic monomer and the hydrophobic monomer is not particularly limited as long as the ratio of the hydrophobic portion of the block copolymer in the outermost surface of the obtained surface lubricating layer is 20 to 45 mol %.

Considering the exhibition of excellent lubricity and durability, the strength of a coating film, firm bonding to the base layer, and the like, when a block copolymer is formed by polymerization, it is preferable that the hydrophilic monomer and the hydrophobic monomer used as raw materials are polymerized in a ratio of 20:1 to 50:1 (hydrophilic monomer:hydrophobic monomer molar ratio), more preferably in a ratio of 25:1 to 45:1. As a result of polymerization in such a ratio, in the block copolymer, the ratio between the hydrophilic portion and the hydrophobic portion that has a reactive functional group can be made within a favorable range. At this time, in the block copolymer used for the formation of a surface lubricating layer, it is preferable that the ratio between the hydrophilic portion and the hydrophobic portion that has a reactive functional group is within a range of 20:1 to 50:1, more preferably within a range of 25:1 to 45:1. Within such a range, the surface lubricating layer can sufficiently exert high lubricity because of the hydrophilic portion, and can also exert high durability (lubricity retention) and coating film strength because of the hydrophobic portion that has a reactive functional group. In particular, considering the improvement of lubricity, the ratio between the hydrophilic portion and the hydrophobic portion that has a reactive functional group is particularly preferably 30:1 to 45:1.

The production method for the block copolymer is not particularly limited, and it may be produced, for example, applying a known polymerization method such as a living radical polymerization method, a polymerization method using a macroinitiator, a polycondensation method or the like. Among them, in terms of the ease of controlling the molecular weight and molecular weight distribution of a hydrophilic-monomer-derived portion or a hydrophobic-monomer-derived portion, it is preferable to use a living radical polymerization method or a polymerization method using a macroinitiator. The living radical polymerization method is not particularly limited, and examples thereof include the methods described in JP-A-11-263819, JP-A-2002-145971, JP-A-2006-316169, and the like, also the atom transfer radical polymerization (ATRP) methods described in J. Am. Chem. Soc., 117, 5614 (1995); Macromolecules, 28, 7901 (1995); Science, 272, 866 (1996); Macromolecules, 31, 5934-5936 (1998); and the like. These methods may be used as they are or with suitable modification. In addition, according to the polymerization method using the macroinitiator, for example, a macroinitiator having a hydrophobic portion that has a reactive functional group and a radically polymerizable group such as a peroxide group or the like is produced, and then the macroinitiator is polymerized with a monomer for forming a hydrophilic portion, whereby a block copolymer having a hydrophilic portion and a hydrophobic portion can be produced.

In addition, for the polymerization to form a block copolymer, known methods such as bulk polymerization, suspension polymerization, emulsion polymerization, solution polymerization and the like may be used. Solvents to be suitably used for polymerization are not particularly limited, and examples include aliphatic organic solvents such as n-hexane, n-heptane, n-octane, n-decane, cyclohexane, methylcyclohexane, liquid paraffin and the like, ethereal solvents such as tetrahydrofuran, dioxane and the like, aromatic organic solvents such as toluene, xylene and the like, halogen organic solvents such as 1,2-dichloroethane, chlorobenzene and the like, polar aprotic organic solvents such as N,N-dimethylformamide, dimethyl sulfoxide and the like. Incidentally, the above solvents may be used alone, and it is also possible to use a mixture of two or more kinds. It is preferable that the concentration of monomers in the polymerization solvent (the total weight concentration of hydrophilic and hydrophobic monomers) is 5 to 90 wt %, more preferably 8 to 80 wt %, and particularly preferably 10 to 50 wt %.

In order to obtain a block copolymer having the desired characteristics, it is preferable that the polymerization temperature is 50 to 100° C., more preferably 55 to 90° C., still more preferably 60 to 85° C., and particularly preferably 65° C. or more and less than 80° C.

In addition, it is preferable that the polymerization time is 1 to 24 hours, more preferably 3 to 12 hours.

For preventing the condensation of the hydrophobic portion in the outermost surface of a surface lubricating layer, it is effective to reduce the heating treatment temperature or increase the ratio of the hydrophilic portion in the block copolymer as described below in detail. However, when the heating treatment temperature is reduced, this results in a decrease in the reaction ratio of the reactive functional group, whereby the durability of the surface lubricating layer tends to decrease. In addition, when the ratio of the hydrophilic portion in the block copolymer is increased, this results in a decrease in the crosslinking density of the surface lubricating layer, whereby similarly the durability of the surface lubricating layer tends to decrease. It has been found that by controlling the solution viscosity (more specifically, the molecular weight) of a block copolymer, the decrease in the durability of a surface lubricating layer caused by the use of a block copolymer having a high ratio of the hydrophilic portion can be suppressed, and also the condensation of the hydrophobic portion in the outermost surface of the surface lubricating layer can be prevented even when the heating treatment temperature is high, whereby excellent lubricity can be exhibited.

That is, the higher the solution viscosity (the higher the molecular weight) of the block copolymer, the more effectively the decrease in the durability of a surface lubricating layer can be suppressed. The solution viscosity of a block copolymer accordingly has a proportional relationship to the molecular weight. Therefore, information about the molecular weight of a block copolymer can be obtained by measuring the viscosity of a solution prepared by dissolving the block copolymer.

More specifically, a 1 wt % chloroform solution of the block copolymer has a viscosity of 8 to 30 mPa·s at a temperature of 30° C. The solution viscosity is measured, by a method in which a block copolymer is dissolved in chloroform to a concentration of 1 wt %, and the viscosity thereof is measured. The viscosity is measured using a Brookfield rotational viscometer. The solution temperature at the time of viscosity measurement is to be 30° C.

When the solution viscosity of the block copolymer is less than 8 mPa·s, in the case where the used block copolymer has a high ratio of the hydrophilic portion, durability is insufficient, and excellent lubricity is difficult to maintain. Meanwhile, when the solution viscosity of the block copolymer is more than 30 mPa·s, the viscosity of a coating liquid at the time of the formation of a surface lubricating layer, that is, during the coating operation, becomes too high, and the surface lubricating layer is likely to be non-uniform, which is undesirable. Therefore, the solution viscosity of the disclosed block copolymer is 8 to 30 mPa·s. The solution viscosity of the block copolymer is more preferably 8 to 27 mPa·s, still more preferably 8 to 25 mPa·s, and particularly preferably 13 to 21 mPa·s.

A block copolymer having the above solution viscosity can be obtained mainly by suitably adjusting the ratio (molar ratio) between the hydrophilic monomer and the hydrophobic monomer used as raw materials for polymerization, the concentration of these monomers (weight concentration: wt %), and the polymerization temperature. There is a tendency that the ratio of the hydrophilic portion and the hydrophobic portion of a block copolymer in the outermost surface of a surface lubricating layer depend mainly on the ratio between the hydrophilic monomer and the reactive monomer (hydrophilic monomer:reactive monomer molar ratio at the time of polymerization) and also on the heating treatment temperature after coating, and the solution viscosity of a block copolymer depends on the concentration of hydrophilic and hydrophobic monomers at the time of polymerization and also on the polymerization temperature. More specifically, there is a tendency that when the concentration of hydrophilic and hydrophobic monomers at the time of polymerization (total weight concentration) is high, the block copolymer has high solution viscosity, and when the polymerization temperature is low, the block copolymer has high solution viscosity.

The following will describe preferred conditions for producing a block copolymer such that the solution viscosity thereof is within the above range (8 to 30 mPa·s), and also the ratio of the hydrophobic portion in the outermost surface of a surface lubricating layer will be within the above range (20 to 45 mol %).

Specifically, it is preferable that the hydrophilic monomer:reactive monomer molar ratio is 20:1 to 50:1, the total concentration of hydrophilic and hydrophobic monomers at the time of polymerization is 8 to 80 wt %, and the polymerization temperature is 55 to 90° C. Here, the hydrophilic monomer:reactive monomer molar ratio is more preferably 25:1 to 45:1, and particularly preferably 30:1 to 45:1, the total concentration of hydrophilic and hydrophobic monomers at the time of polymerization is more preferably 10 to 50 wt %, and the polymerization temperature is more preferably 60 to 85° C.

The method for producing a medical device (method for forming a lubricating coating film (surface lubricating layer)) requires the use of the disclosed block copolymer, but is otherwise not particularly limited, and a known method may be applied as it is or with suitable modification.

A specific example thereof is a method in which the block copolymer is dissolved in a solvent to prepare a coating liquid (lubricating coating agent, coating liquid), the coating liquid is applied onto a base layer to form an application layer, and then the application layer is subjected to a heating treatment to cause a crosslinking reaction of the block copolymer, thereby forming a surface lubricating layer. That is, it is preferable that the method for forming a surface lubricating layer at least includes a lubricating coating agent coating step, in which a lubricating coating agent is applied onto a base layer, and a heating step, in which an application layer made of the lubricating coating agent is subjected to a heating treatment. By such a method, lubricity and durability can be imparted to the surface of a medical device.

In the above method, the solvent used for dissolving the block copolymer is not particularly limited as long as it is capable of dissolving the disclosed block copolymer. Specific examples thereof include, but are not limited to, water, alcohols such as methanol, ethanol, isopropanol, ethylene glycol and the like, ketones such as acetone, methyl ethyl ketone and the like, esters such as ethyl acetate and the like, halides such as chloroform and the like, olefins such as hexane and the like, ethers such as tetrahydrofuran, butyl ether and the like, aromatics such as benzene, toluene and the like, and amides such as N,N-dimethylformamide (DMF) and the like. They may be used alone, and it is also possible to use two or more kinds together.

The concentration of the block copolymer in a coating liquid is not particularly limited. In terms of application properties and desired effects (lubricity and durability) that can be obtained, for example, the concentration of the block copolymer in a coating liquid is 0.01 to 20 wt %, more preferably 0.05 to 15 wt %, and still more preferably 0.1 to 10 wt %. When the concentration of the block copolymer is within the above range, the lubricity and durability of the resulting surface lubricating layer can be sufficiently exerted. In addition, a surface lubricating layer having a desired uniform thickness can be easily obtained by a single coating, and this is preferable in terms of operability (e.g., the ease of coating) and production efficiency. However, a concentration outside the above range is sufficiently usable unless the operation effect is adversely affected.

The method for applying a coating liquid to the surface of a base layer is not particularly limited, and it is possible to apply a known method, such as an application/printing method, an immersion method (dipping, dip coating), an atomization method (spraying), a spin coating method, a coating method using a sponge impregnated with a mixed solution, or the like. Among them, it is preferable to use an immersion method (dipping, dip coating).

Incidentally, in the case of forming a surface lubricating layer on a thin and narrow inner surface of a catheter, a guidewire, an injection needle, or the like, it is possible that the base layer is immersed in a coating liquid, and then the pressure in the system is reduced to cause degassing. When the pressure is reduced to cause degassing, the thin and narrow inner surface can be quickly impregnated with the solution, whereby the formation of a surface lubricating layer can be promoted.

In addition, in the case of forming a surface lubricating layer on only part of a base layer, only part of the base layer is immersed in a coating liquid to form a coating of the coating liquid on part of the base layer, whereby a surface lubricating layer can be formed on a desired portion of the surface of the base layer.

In the case where it is difficult to immerse only part of a base layer in a coating liquid, it is possible that a part of the surface of a base layer, where a surface lubricating layer does not have to be formed, is previously protected (covered or the like) with an appropriate member or material that can be attached/detached (mounted/dismounted), then the base layer is immersed in a coating liquid to form a coating of the coating liquid on the base layer, and the protective member (material) on the part of the surface of the base layer, where a surface lubricating layer does not have to be formed, is removed, followed by a heating treatment or the like, thereby forming a surface lubricating layer on a desired portion of the surface of the base layer. However, the formation methods are not limited to these methods, and a surface lubricating layer can be formed suitably using a conventionally known method. For example, in the case where it is difficult to immerse only part of a base layer in a mixed solution, in place of the immersion method, it is also possible to apply other coating techniques (e.g., a method in which a coating liquid is applied to a predetermined part of the surface of a medical device using an application apparatus such as a spraying apparatus, a bar coater, a die coater, a reverse coater, a comma coater, a gravure coater, a spray coater, a doctor knife or the like). Incidentally, in the case where the structure of the medical device requires both outer and inner surfaces of a cylindrical instrument to have a surface lubricating layer, it is preferable to use an immersion method (dipping) because both outer and inner surfaces can be coated at once.

After a base layer is immersed in a coating liquid containing the block copolymer in this manner, the base layer is removed from the coating liquid and subjected to a heating treatment. Here, the heating treatment conditions (temperature, time, and the like) are not particularly limited as long as the conditions allow for the formation of a surface lubricating layer containing the block copolymer on the base layer. Specifically, it is preferable that the heating temperature is 60 to 200° C., more preferably 80 to 160° C., still more preferably more than 80° C. and 150° C. or less, and particularly preferably is 90 to 140° C. In addition, it is preferable that the heating time is 15 minutes to 24 hours, more preferably 1 to 10 hours. When the conditions are as above, the ratio of the hydrophobic portion of the block copolymer in an outermost surface of the surface lubricating layer can be easily made within a range of 20 to 45 mol %. In addition, when the heating conditions are as above, the reactive functional group of the block copolymer undergoes a crosslinking reaction, whereby a firm surface lubricating layer that does not easily peel off the base layer can be formed.

From the above, it is preferable that the disclosed medical device is produced by a method that includes polymerizing a compound including a hydrophilic portion (hydrophilic monomer) and a compound including a hydrophobic portion that has a reactive functional group (hydrophobic monomer) in a molar ratio of 20:1 to 50:1 to give a block copolymer whose 1 wt % chloroform solution has a viscosity of 8 to 30 mPa·s at a temperature of 30° C.; preparing a coating liquid containing the block copolymer; and applying the coating liquid onto a base layer, followed by a heating treatment at a temperature within a range of 60 to 200° C., thereby forming a surface lubricating layer having an outermost surface in which the ratio of the hydrophobic portion of the block copolymer is 20 to 45 mol %. At this time, the preferred ranges of the mixing ratio (molar ratio) between the hydrophilic monomer and the hydrophobic monomer used as raw materials, the solution viscosity of the block copolymer, and the temperature in the heating treatment after the application of the coating liquid are as described above.

Incidentally, in the case where the reactive functional group is an epoxy group, although an epoxy group can be self-crosslinked by heating, in order to promote the crosslinking reaction, the coating solution may also contain an epoxy reaction catalyst or a polyfunctional crosslinking agent that can react with an epoxy group.

In addition, pressure conditions for the heating treatment are not limited either. The treatment may be performed under ambient pressure (atmospheric pressure) or under increased pressure or reduced pressure.

As a heating treatment means (apparatus), it is possible to use an oven, a vacuum dryer, or the like.

By the above method in which a coating film (application layer) of the block copolymer is formed on the surface of a base layer, and then a reactive functional group is crosslinked, a firm surface lubricating layer that does not easily peel off the base layer can be formed. Accordingly, the disclosed medical device can exert excellent lubricity and durability.

The medical device 10 is a device that is used in contact with a body fluid, blood, or the like. The surface thereof has lubricity in a body fluid or an aqueous liquid such as physiological saline or the like, making it possible to improve the operability or reduce the damage to mucous membranes. Specific examples thereof include catheters, guidewires, indwelling needles, and the like used in blood vessels, and also include the following medical devices.

(a) Catheters orally or transnasally inserted into or indwelled in digestive organs, such as stomach tube catheters, nutrition catheters, feeding tubes and the like.

(b) Catheters orally or transnasally inserted into or indwelled in the respiratory tract or trachea, such as oxygen catheters, oxygen cannulas, tubes and cuffs of tracheal tubes, tubes and cuffs of tracheotomy tubes, tracheal suction catheters and the like.

(c) Catheters inserted into or indwelled in the urethra or ureter, such as urethral catheters, urine drainage catheters, catheters and balloons of urethral balloon catheters and the like.

(d) Catheters inserted into or indwelled in various body cavities, organs, and tissues, such as suction catheters, drainage catheters, rectum catheters and the like.

(e) Catheters inserted into or indwelled in blood vessels, such as indwelling needles, IVH catheters, thermodilution catheters, angiographic catheters, and vasodilatation catheters, dilators, introducers and the like; and guidewires, stylets, and the like for these catheters.

(f) Artificial tracheas, artificial bronchi, and the like.

(g) Medical devices for extracorporeal circulation therapies (artificial lungs, artificial hearts, artificial kidneys, and the like) and circuits therefor.

Advantageous effects will be described hereinafter through examples and comparative examples. However, the technical scope of the invention is not limited to the following examples.

1. Production of Block Copolymer (Block Copolymer 1)

29.7 g of triethylene glycol was added dropwise to 72.3 g of adipic acid dichloride at 50° C., and then hydrochloric acid was removed under reduced pressure at 50° C. for 3 hours. To 22.5 g of the resulting oligoester was added 4.5 g of methyl ethyl ketone, and the mixture was added dropwise to a solution containing 5 g of sodium hydroxide, 6.93 g of 31% hydrogen peroxide, 0.44 g of dioctyl phosphate (surfactant), and 120 g of water and allowed to react at −5° C. for 20 minutes. The obtained product was repeatedly washed with water and with methanol, and then dried to give a polyperoxide (PPO) having a plurality of peroxide groups in the molecule. Subsequently, 0.5 g of the PPO as a polymerization initiator, 9.5 g of glycidyl methacrylate (GMA) as a hydrophobic monomer, and benzene as a solvent were stirred under reduced pressure at 65° C. for 2 hours to cause polymerization. The reaction product was reprecipitated with diethyl ether to give poly-GMA (PPO-GMA) having peroxide groups in the molecule.

Subsequently, 1.35 g of the obtained PPO-GMA (9.5 mmol as GMA) as a polymerization initiator was dissolved in chlorobenzene together with 11.2 g of N,N-dimethylacrylamide (DMAA) (113 mmol) as a hydrophilic monomer and heated in a nitrogen atmosphere for 7 hours to 80° C. to cause polymerization. The concentration of PPO-GMA and the concentration of DMAA dissolved at the time of polymerization are as shown in Table 1. The reaction product was reprecipitated with cyclohexane and recovered, thereby producing a block copolymer 1 having a DMAA portion as a hydrophilic portion and a GMA portion as a hydrophobic portion. The DMAA:GMA ratio of the produced block copolymer 1 was measured by $^1$H-NMR. As a result, the DMAA:GMA ratio (i.e., the molar ratio between the hydrophilic portion and the hydrophobic portion in the block copolymer) was 12:1 (molar ratio). The obtained block copolymer 1 was also measured for the viscosity of its 1 wt % chloroform solution in a 30° C. environment using a Brookfield rotational viscometer (manufactured by Brookfield Inc., apparatus name: DV-I Prime). The result was 6.0 mPa·s.

(Block Copolymer 2)

0.61 g of PPO-GMA (4.3 mmol as GMA) obtained in the same manner as for the block copolymer 1 was dissolved as a polymerization initiator in chlorobenzene together with 11.3 g of DMAA (114 mmol) and heated in a nitrogen atmosphere for 7 hours to 90° C. to cause polymerization, thereby giving a block copolymer 2. The DMAA:GMA ratio (molar ratio) of the produced block copolymer 2 measured in the same manner as for the block copolymer 1 was 28:1

(molar ratio). At this time, the solution viscosity of the block copolymer 2 measured in the same manner as for the block copolymer 1 was 4.2 mPa·s.

(Block Copolymer 3)

0.60 g of PPO-GMA (4.2 mmol as GMA) obtained in the same manner as for the block copolymer 1 was dissolved as a polymerization initiator in chlorobenzene together with 10.1 g of DMAA (102 mmol) and heated in a nitrogen atmosphere for 7 hours to 75° C. to cause polymerization, thereby giving a block copolymer 3.

The DMAA:GMA ratio (molar ratio) of the produced block copolymer 3 measured in the same manner as for the block copolymer 1 was 29:1 (molar ratio). At this time, the solution viscosity of the block copolymer 3 measured in the same manner as for the block copolymer 1 was 14.0 mPa·s.

(Block Copolymer 4)

0.65 g of PPO-GMA (4.6 mmol as GMA) obtained in the same manner as for the block copolymer 1 was dissolved as a polymerization initiator in chlorobenzene together with 10.0 g of DMAA (101 mmol) and heated in a nitrogen atmosphere for 7 hours to 70° C. to cause polymerization, thereby giving a block copolymer 4. The DMAA:GMA ratio (molar ratio) of the produced block copolymer 4 measured in the same manner as for the block copolymer 1 was 28:1 (molar ratio). At this time, the solution viscosity of the block copolymer 4 measured in the same manner as for the block copolymer 1 was 20.2 mPa·s.

(Block Copolymer 5)

0.42 g of PPO-GMA (3.0 mmol as GMA) obtained in the same manner as for the block copolymer 1 was dissolved as a polymerization initiator in chlorobenzene together with 10.0 g of DMAA (101 mmol) and heated in a nitrogen atmosphere for 7 hours to 75° C. to cause polymerization, thereby giving a block copolymer 5. The DMAA:GMA ratio (molar ratio) of the produced block copolymer 5 measured in the same manner as for the block copolymer 1 was 36:1 (molar ratio). At this time, the solution viscosity of the block copolymer 5 measured in the same manner as for the block copolymer 1 was 11.8 mPa·s.

(Block Copolymer 6)

0.49 g of PPO-GMA (3.5 mmol as GMA) obtained in the same manner as for the block copolymer 1 was dissolved as a polymerization initiator in chlorobenzene together with 12.0 g of DMAA (121 mmol) and heated in a nitrogen atmosphere for 7 hours to 85° C. to cause polymerization, thereby giving a block copolymer 6. The DMAA:GMA ratio (molar ratio) of the produced block copolymer 6 measured in the same manner as for the block copolymer 1 was 38:1 (molar ratio). At this time, the solution viscosity of the block copolymer 6 measured in the same manner as for the block copolymer 1 was 8.2 mPa·s.

(Block Copolymer 7)

0.36 g of PPO-GMA (2.5 mmol as GMA) obtained in the same manner as for the block copolymer 1 was dissolved as a polymerization initiator in chlorobenzene together with 10.1 g of DMAA (102 mmol) and heated in a nitrogen atmosphere for 7 hours to 75° C. to cause polymerization, thereby giving a block copolymer 7.

The DMAA:GMA ratio (molar ratio) of the produced block copolymer 6 measured in the same manner as for the block copolymer 1 was 44:1 (molar ratio). At this time, the viscosity of the block copolymer 7 measured in the same manner as for the block copolymer 1 was 8.8 mPa·s.

(Block Copolymer 8)

0.24 g of PPO-GMA (1.7 mmol as GMA) obtained in the same manner as for the block copolymer 1 was dissolved as a polymerization initiator in chlorobenzene together with 10.1 g of DMAA (102 mmol) and heated in a nitrogen atmosphere for 7 hours to 75° C. to cause polymerization, thereby giving a block copolymer 8.

The DMAA:GMA ratio (molar ratio) of the produced block copolymer 8 measured in the same manner as for the block copolymer 1 was 66:1 (molar ratio). At this time, the viscosity of the block copolymer 8 measured in the same manner as for the block copolymer 1 was 8.2 mPa·s.

TABLE 1

Polymerization Conditions for Each Block Copolymer and Results of $^1$H-NMR Measurement of DMAA:GMA Ratio and Solution Viscosity

| Sample No. | PPO-GMA Concentration [wt %] | DMAA Concentration [wt %] | Polymerization Temperature [° C.] | DMAA:GMA Ratio | Solution Viscosity [mPa · s] |
|---|---|---|---|---|---|
| Block Copolymer 1 | 1.35 | 11.2 | 80 | 12:1 | 6.0 |
| Block Copolymer 2 | 0.61 | 11.3 | 90 | 28:1 | 4.2 |
| Block Copolymer 3 | 0.60 | 10.1 | 75 | 29:1 | 14.0 |
| Block Copolymer 4 | 0.65 | 10.0 | 70 | 28:1 | 20.2 |
| Block Copolymer 5 | 0.42 | 10.0 | 75 | 36:1 | 11.8 |
| Block Copolymer 6 | 0.49 | 12.0 | 85 | 38:1 | 8.2 |
| Block Copolymer 7 | 0.36 | 10.1 | 75 | 44:1 | 8.8 |
| Block Copolymer 8 | 0.24 | 10.1 | 75 | 66:1 | 8.2 |

2. Production of Lubricating Coating Sample (Formation of Surface Lubricating Layer)

Example 1: Lubricating Coating Sample 1

The block copolymer 3 obtained as above was dissolved in DMF to a concentration of 3 wt % to give a coating liquid. A 15 mm×50 mm×1 mm press sheet of a Nylon® elastomer (ELG 5660, manufactured by EMS CHEMIE Ltd.) was dip-coated with the coating liquid produced as above and then subjected to a heating treatment at 130° C. for 3 hours to form a surface lubricating layer on the sheet, thereby giving a lubricating coating sample 1.

The chemical composition of the outermost surface of the lubricating coating layer of the lubricating coating sample 1 produced as above was measured by XPS (apparatus: Quantera STM manufactured by ULVAC-PHI Inc., X-ray beam: 50 W, 15 kV; ϕ 200 μm, signal capturing angle: 10°) to calculate the proportion of GMA present in the outermost surface of the surface lubricating layer in the lubricating coating sample 1. Incidentally, the XPS measurement range (measurement depth) is the electron inelastic mean free path, which is calculated to be a depth of 2 nm under the above measurement conditions. At this time, the ratio of GMA-derived hydrophobic portion measured by XPS was 38 mol % (incidentally, the ratio of DMAA-derived hydrophilic portion was 62 mol %).

The ratio of the hydrophilic portion and the hydrophobic portion were determined by XPS as follows.

First, carbon atoms (C) and nitrogen atoms (N) contained in the outermost surface of a surface lubricating layer (a region to a depth of 2 nm) were quantitatively analyzed by XPS from the peak area to determine the ratio of the number of carbon atoms to the number of nitrogen atoms ($n_C/n_N$). At this time, for carbon atoms, the photoelectron peak intensity from the C1s level was analyzed, while for nitrogen atoms, the photoelectron peak intensity from the N1s level was analyzed.

Here, the number of carbon atoms in DMAA forming a hydrophilic portion is 5, and the number of carbon atoms in GMA forming a hydrophobic portion is 7, while the number of nitrogen atoms in DMAA is 1, and the number of nitrogen atoms in GMA is 0. Therefore, the following equations (1) and (2) are true.

$$n_C = 5p + 7q \quad (1)$$

$$n_N = p \quad (2)$$

In the equations, "p" is the number of molecules of DMAA in the block copolymer within the analysis range (precisely, the number of DMAA-derived hydrophilic portions), while "q" is the number of molecules of GMA (precisely, the number of GMA-derived hydrophobic portions).

From the equations (1) and (2), the following equation (3) can be derived.

$$n_C/n_N = 5 + 7(q/p) \quad (3)$$

As mentioned above, the ratio of the number of carbon atoms to the number of nitrogen atoms ($n_C/n_N$) is calculated by XPS measurement. Thus, by substituting this into the equation (3), "q/p", that is, the ratio of the number of hydrophilic portions to the number of hydrophobic portions in a block copolymer, can be calculated. Here, considering that the total of the ratio of the hydrophilic portion and the ratio of the hydrophobic portion is 1 (100 mol %), the ratio of the hydrophobic portion and the ratio of the hydrophilic portion were each determined.

Incidentally, although carbon atoms and nitrogen atoms were selected as the object to be analyzed by XPS measurement in this example, the ratios of the hydrophobic portion and the hydrophilic portion in a block copolymer can be derived by the above method using any two kinds of elements that can be measured by XPS.

Example 2: Lubricating Coating Sample 2

A lubricating coating sample 2 was produced in the same manner as for the lubricating coating sample 1, except that the block copolymer 3 was changed to the block copolymer 4. With respect to the obtained lubricating coating sample 2, the proportion of GMA present in the outermost surface of the surface lubricating layer was measured using XPS. At this time, the ratio of GMA-derived hydrophobic portion measured by XPS was 37 mol % (incidentally, the ratio of DMAA-derived hydrophilic portion was 63 mol %).

Example 3: Lubricating Coating Sample 3

A lubricating coating sample 3 was produced in the same manner as for the lubricating coating sample 1, except that the block copolymer 3 was changed to the block copolymer 5. With respect to the obtained lubricating coating sample 3, the proportion of GMA present in the outermost surface of the surface lubricating layer was measured using XPS. At this time, the ratio of GMA-derived hydrophobic portion measured by XPS was 31 mol % (incidentally, the ratio of DMAA-derived hydrophilic portion was 69 mol %).

Example 4: Lubricating Coating Sample 4

A lubricating coating sample 4 was produced in the same manner as for the lubricating coating sample 1, except that the block copolymer 3 was changed to the block copolymer 5, and that the temperature of the heating treatment after dip coating with a coating liquid was changed to 80° C. With respect to the obtained lubricating coating sample 4, the proportion of GMA present in the outermost surface of the surface lubricating layer was measured using XPS. At this time, the ratio of GMA-derived hydrophobic portion measured by XPS was 21 mol % (incidentally, the ratio of DMAA-derived hydrophilic portion was 79 mol %).

Example 5: Lubricating Coating Sample 5

A lubricating coating sample 5 was produced in the same manner as for the lubricating coating sample 1, except that the block copolymer 3 was changed to the block copolymer 6. With respect to the obtained lubricating coating sample 5, the proportion of GMA present in the outermost surface of the surface lubricating layer was measured using XPS. At this time, the ratio of GMA-derived hydrophobic portion measured by XPS was 30 mol % (incidentally, the ratio of DMAA-derived hydrophilic portion was 70 mol %).

Example 6: Lubricating Coating Sample 6

A lubricating coating sample 6 was produced in the same manner as for the lubricating coating sample 1, except that the block copolymer 3 was changed to the block copolymer 7. With respect to the obtained lubricating coating sample 4, the proportion of GMA present in the outermost surface of the surface lubricating layer was measured using XPS. At this time, the ratio of GMA-derived hydrophobic portion measured by XPS was 27 mol % (incidentally, the ratio of DMAA-derived hydrophilic portion was 73 mol %).

Comparative Example 1: Lubricating Coating Sample 7

A lubricating coating sample 7 was produced in the same manner as for the lubricating coating sample 1, except that the block copolymer 3 was changed to the block copolymer 1. With respect to the obtained lubricating coating sample 7, the proportion of GMA present in the outermost surface of the surface lubricating layer was measured using XPS. At this time, the ratio of GMA-derived hydrophobic portion measured by XPS was 51 mol % (incidentally, the ratio of DMAA-derived hydrophilic portion was 49 mol %).

Comparative Example 2: Lubricating Coating Sample 8

A lubricating coating sample 8 was produced in the same manner as for the lubricating coating sample 1, except that the block copolymer 3 was changed to the block copolymer 1, and that the temperature of the heating treatment after dip coating with a coating liquid was changed to 80° C. With respect to the obtained lubricating coating sample 8, the proportion of GMA present in the outermost surface of the surface lubricating layer was measured using XPS. At this time, the ratio of GMA-derived hydrophobic portion measured by XPS was 29 mol % (incidentally, the ratio of DMAA-derived hydrophilic portion was 71 mol %).

Comparative Example 3: Lubricating Coating Sample 9

A lubricating coating sample 9 was produced in the same manner as for the lubricating coating sample 1, except that the block copolymer 3 was changed to the block copolymer 2. With respect to the obtained lubricating coating sample 9, the proportion of GMA present in the outermost surface of the surface lubricating layer was measured using XPS. At this time, the ratio of GMA-derived hydrophobic portion measured by XPS was 36 mol % (incidentally, the ratio of DMAA-derived hydrophilic portion was 64 mol %).

Comparative Example 4: Lubricating Coating Sample 10

A lubricating coating sample 10 was produced in the same manner as for the lubricating coating sample 1, except that the block copolymer 3 was changed to the block copolymer 8. With respect to the obtained lubricating coating sample 10, the proportion of GMA present in the outermost surface of the surface lubricating layer was measured using XPS. At this time, the ratio of GMA-derived hydrophobic portion measured by XPS was 16 mol % (incidentally, the ratio of DMAA-derived hydrophilic portion was 84 mol %).

Evaluation of Lubricity and Durability of Surface Lubricating Layer

Figure 3:
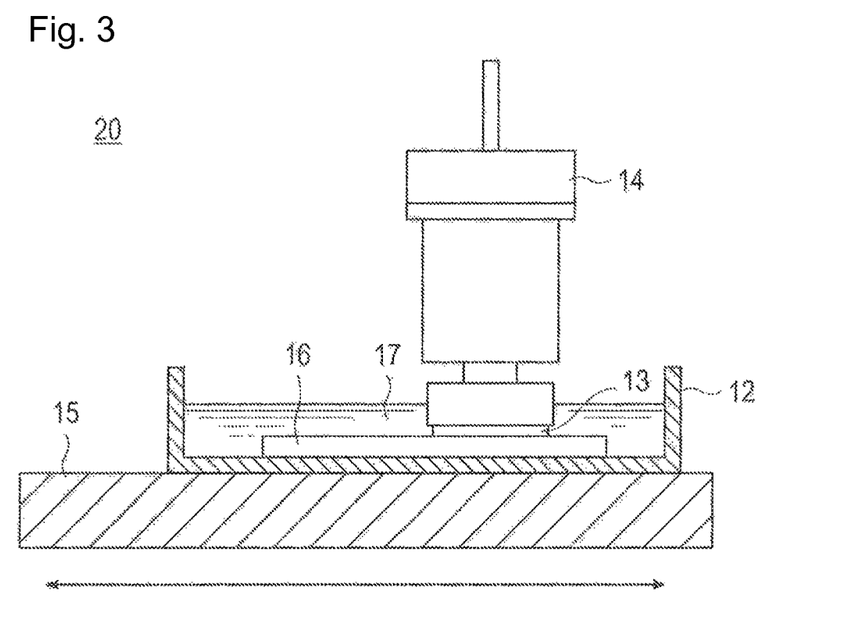
FIG. 3 is a schematic diagram of a surface lubricity retention evaluation tester (friction tester) used in the examples and comparative examples.

With respect to each of the lubricating coating samples (hereinafter sometimes simply referred to as "samples") obtained above in Examples 1 to 6 and Comparative Examples 1 to 4, the lubricity and durability of the surface lubricating layer were evaluated using a friction tester 20 shown in FIG. 3 (manufactured by Trinity-Lab Inc., Handy Tribo Master TL201) by the following method. That is, each sample 16 was fixed in a petri dish 12 and immersed in a height of water 17 that soaks the entire sample 16. The petri dish 12 was placed on a moving table 15 of the friction tester 20 shown in FIG. 3. A cylindrical polyethylene terminal ($\phi$=10 mm, R=1 mm) 13 was brought into contact with the sample 16, and a load 14 of 450 g was applied to the terminal. The moving table 15 was horizontally moved back and forth 50 times at a rate of 100 cm/min and a moving distance of 2 cm, and the resulting sliding resistance was measured. Sliding resistance after one back-and-forth movement and that after 50 back-and-forth movements were recorded and defined as initial sliding resistance and post-test sliding resistance, respectively. The results are shown in Table 2.

TABLE 2

Production Conditions for Each Sample and Results of XPS Evaluation of GMA Proportion and Lubrication Durability

| | Sample No. | Block Copolymer | Heating Temperature [° C.] | GMA Proportion in Outermost Surface [mol %] | Initial Sliding Resistance [gf] | Post-Test Sliding Resistance [gf] |
|---|---|---|---|---|---|---|
| Example 1 | Lubricating coating sample 1 | Block Copolymer 3 | 130 | 38 | 12 | 12 |
| Example 2 | Lubricating coating sample 2 | Block Copolymer 4 | 130 | 37 | 12 | 15 |
| Example 3 | Lubricating coating sample 3 | Block Copolymer 5 | 130 | 31 | 9 | 14 |
| Example 4 | Lubricating coating sample 4 | Block Copolymer 5 | 80 | 21 | 8 | 20 |
| Example 5 | Lubricating coating sample 5 | Block Copolymer 6 | 130 | 30 | 9 | 12 |
| Example 6 | Lubricating coating sample 6 | Block Copolymer 7 | 130 | 27 | 9 | 13 |
| Comparative Example 1 | Lubricating coating sample 7 | Block Copolymer 1 | 130 | 51 | 22 | 35 |
| Comparative Example 2 | Lubricating coating sample 8 | Block Copolymer 1 | 80 | 29 | 13 | 112 |
| Comparative Example 3 | Lubricating coating sample 9 | Block Copolymer 2 | 130 | 36 | 12 | 64 |
| Comparative Example 4 | Lubricating coating sample 10 | Block Copolymer 8 | 130 | 16 | 6 | 99 |

In Examples 1 to 6, all the samples showed excellent lubricity from the first time, and the excellent lubricity was maintained even after the test of sliding back and forth 50 times. In addition, among the examples, in Examples 1 and 2, there was no significant difference between the initial sliding resistance and the post-test sliding resistance, indicating extremely excellent durability. These results suggest that when a block copolymer having a viscosity like those of the block copolymers 3 and 4 (14.0 to 20.2 mPa·s) is used, particularly excellent durability can be obtained. Further, among the examples, the initial sliding resistance is extremely small in Examples 3 to 6. This suggests that when a block copolymer having a hydrophilic monomer/hydrophobic monomer ratio like those of the block copolymers 5 to 7 (36:1 to 44:1) is used, excellent lubricity can be obtained.

Meanwhile, in Comparative Example 1, there was a pronounced condensation of GMA in the outermost surface of the surface lubricating layer, and the initial lubricity was apparently lower than in Examples 1 to 6.

In Comparative Example 2, because the heating treatment temperature was lower than in Comparative Example 1, the condensation of GMA in the outermost surface of the lubricating coating layer could be suppressed, and the initial lubricity was excellent. However, as a result of sliding back and forth 50 times, the surface lubricating layer easily peeled off, and the post-test sliding resistance was significantly high.

In Comparative Example 3, because the ratio of the hydrophilic portion of the block copolymer 2 was high, the condensation of GMA in the outermost surface of the surface lubricating layer could be suppressed. However, the surface lubricating layer peeled off as a result of sliding back and forth 50 times, and the post-test sliding resistance was high. In contrast, in Example 1 and Example 2, where the GMA proportion in the outermost surface is almost equal to that in Comparative Example 3, and only the solution viscosity is significantly different, excellent durability was shown.

In Comparative Example 4, because the ratio of the hydrophilic portion of the block copolymer 8 was extremely high, the condensation of GMA in the outermost surface of the lubricating coating layer could be substantially suppressed. However, because the number of reactive functional groups was too small, the surface lubricating layer easily peeled off as a result of sliding back and forth 50 times, and the post-test sliding resistance was significantly high.

The above results show that a medical device as disclosed above including a surface lubricating layer formed from the block copolymer can exhibit improved lubricity. Further, it is shown that the surface lubricating layer does not easily peel off, and its lubricity can be permanently exhibited.

The detailed description above describes a medical device and method for producing a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

REFERENCE SIGNS LIST

1: Base layer
1a: Base layer core part
1b: Base surface layer
2: Surface lubricating layer
10: Medical device
12: Petri dish
13: Cylindrical polyethylene terminal
14: Load
15: Moving table
16: Lubricating coating sample (sample)
17: Water
20: Friction tester

What is claimed is:

1. A medical device comprising, on a base layer, a surface lubricating layer formed from a block copolymer having a hydrophilic portion and a hydrophobic portion that has a reactive functional group, wherein
the ratio of the hydrophobic portion of the block copolymer in an outermost surface of the surface lubricating layer being 20 to 45 mol %, and
the viscosity of a 1 wt % chloroform solution of the block copolymer at a temperature of 30° C. being 8 to 30 mPa·s.

2. The medical device according to claim 1, wherein the ratio between the hydrophilic portion and the hydrophobic portion that has a reactive functional group of the block copolymer used to form the surface lubricating layer is within a range of 20:1 to 50:1.

3. The medical device according to claim 2, wherein the hydrophilic portion is derived from at least one member selected from the group consisting of acrylic acid, methacrylic acid, N-methylacrylamide, N,N-dimethylacrylamide, acrylamide, acryloylmorpholine, N,N-dimethylamino ethyl acrylate, vinylpyrrolidone, 2-methacryloyloxyethyl phosphorylcholine, 2-methacryloyloxyethyl-D-glycoside, 2-methacryloyloxyethyl-D-mannoside, vinyl methyl ether, 2-hydroxyethyl (meth)acrylate, 4-hydroxybutyl (meth)acrylate, 2-hydroxypropyl (meth)acrylate, 2-hydroxybutyl (meth)acrylate, 6-hydroxyhexyl (meth)acrylate, 1,4-cyclohexanedimethanol mono(meth)acrylate, 1-chloro-2-hydroxypropyl (meth)acrylate, diethylene glycol mono(meth)acrylate, 1,6-hexanediol mono(meth)acrylate, pentaerythritol tri(meth)acrylate, dipentaerythritol penta(meth)acrylate, neopentyl glycol mono(meth)acrylate, trimethylolpropane di(meth)acrylate, trimethylolethane di(meth)acrylate, 2-hydroxy-3-phenoxypropyl (meth)acrylate, 2-hydroxycyclohexyl (meth)acrylate, 4-hydroxycyclohexyl (meth)acrylate, cyclohexanedimethanol mono(meth)acrylate, poly(ethylene glycol) methyl ether acrylate, and poly (ethylene glycol) methyl ether methacrylate.

4. The medical device according to claim 1, wherein the hydrophilic portion is derived from at least one member selected from the group consisting of acrylic acid, methacrylic acid, N-methylacrylamide, N,N-dimethylacrylamide, acrylamide, acryloylmorpholine, N,N-dimethylamino ethyl acrylate, vinylpyrrolidone, 2-methacryloyloxyethyl phosphorylcholine, 2-methacryloyloxyethyl-D-glycoside, 2-methacryloyloxyethyl-D-mannoside, vinyl methyl ether, 2-hydroxyethyl (meth)acrylate, 4-hydroxybutyl (meth)acrylate, 2-hydroxypropyl (meth)acrylate, 2-hydroxybutyl (meth)acrylate, 6-hydroxyhexyl (meth)acrylate, 1,4-cyclohexanedimethanol mono(meth)acrylate, 1-chloro-2-hydroxypropyl (meth)acrylate, diethylene glycol mono(meth)acrylate, 1,6-hexanediol mono(meth)acrylate, pentaerythritol tri(meth)acrylate, dipentaerythritol penta(meth)acrylate, neopentyl glycol mono(meth)acrylate, trimethylolpropane di(meth)acrylate, trimethylolethane di(meth)acrylate, 2-hydroxy-3-phenoxypropyl (meth)acrylate, 2-hydroxycyclohexyl (meth)acrylate, 4-hydroxycyclohexyl (meth)acrylate, cyclohexanedimethanol mono(meth)acrylate, poly(ethylene glycol) methyl ether acrylate, and poly(ethylene glycol) methyl ether methacrylate.

5. The medical device according to claim 4, wherein the hydrophobic portion is derived from at least one member selected from the group consisting of glycidyl acrylate, glycidyl methacrylate, allyl glycidyl ether, acryloyloxymethyl isocyanate, acryloyloxyethyl isocyanate, methacryloyloxy methyl isocyanate, methacryloyloxy ethyl isocyanate, crotonaldehyde, acrolein, and methacrolein.

6. The medical device according to claim 3, wherein the hydrophobic portion is derived from at least one member selected from the group consisting of glycidyl acrylate, glycidyl methacrylate, allyl glycidyl ether, acryloyloxymethyl isocyanate, acryloyloxyethyl isocyanate, methacryloyloxy methyl isocyanate, methacryloyloxy ethyl isocyanate, crotonaldehyde, acrolein, and methacrolein.

7. The medical device according to claim 2, wherein the hydrophobic portion is derived from at least one member selected from the group consisting of glycidyl acrylate, glycidyl methacrylate, allyl glycidyl ether, acryloyloxymethyl isocyanate, acryloyloxyethyl isocyanate, methacryloyloxy methyl isocyanate, methacryloyloxy ethyl isocyanate, crotonaldehyde, acrolein, and methacrolein.

8. The medical device according to claim 1, wherein the hydrophobic portion is derived from at least one member selected from the group consisting of glycidyl acrylate, glycidyl methacrylate, allyl glycidyl ether, acryloyloxymethyl isocyanate, acryloyloxyethyl isocyanate, methacryloyloxy methyl isocyanate, methacryloyloxy ethyl isocyanate, crotonaldehyde, acrolein, and methacrolein.

9. The medical device according to claim 1, wherein the ratio between the hydrophilic portion and the hydrophobic portion that has a reactive functional group of the block copolymer used to form the surface lubricating layer is within a range of 25:1 to 45:1.

10. The medical device according to claim 1, wherein the ratio between the hydrophilic portion and the hydrophobic portion that has a reactive functional group of the block copolymer used to form the surface lubricating layer is within a range of 30:1 to 45:1.

11. The medical device according to claim 1, wherein the viscosity of a 1 wt % chloroform solution of the block copolymer at a temperature of 30° C. is 8 to 27 mPa·s.

12. The medical device according to claim 1, wherein the viscosity of a 1 wt % chloroform solution of the block copolymer at a temperature of 30° C. is 13 to 21 mPa·s.

13. A method for producing a medical device, comprising:
polymerizing a compound including a hydrophilic portion and a compound including a hydrophobic portion that has a reactive functional group in a molar ratio of 20:1 to 50:1 to give a block copolymer whose 1 wt % chloroform solution has a viscosity of 8 to 30 mPa·s at a temperature of 30° C.;
preparing a coating liquid containing the block copolymer; and
applying the coating liquid onto a base layer, followed by a heating treatment at a temperature within a range of 60 to 200° C., thereby forming a surface lubricating layer having an outermost surface in which the ratio of the hydrophobic portion of the block copolymer is 20 to 45 mol %.

14. The method for producing a medical device according to claim 13, wherein the polymerization temperature is 50 to 100° C.

15. The method for producing a medical device according to claim 13, wherein the polymerization temperature is 60 to 85° C.

16. The method for producing a medical device according to claim 13, wherein the molar ratio of the compound including a hydrophilic portion to the compound including a hydrophobic portion is 20:1 to 50:1.

17. The method for producing a medical device according to claim 13, wherein the concentration of the block copolymer in the coating liquid is 0.01 to 20 wt %.

18. The method for producing a medical device according to claim 13, wherein the heating treatment temperature is 80 to 160° C.

19. The method for producing a medical device according to claim 13, wherein the heating treatment temperature is 90 to 140° C.

20. The method for producing a medical device according to claim 13, wherein the heating treatment time is 1 to 10 hours.

21. The medical device according to claim 1, wherein the hydrophobic portion is condensed near an outermost surface of the surface lubricating layer.

* * * * *